United States Patent
Small et al.

(10) Patent No.: US 6,235,242 B1
(45) Date of Patent: May 22, 2001

(54) SAMPLE SIZE CHARACTERIZATION TECHNIQUE AND APPARATUS FOR LIQUID ANALYSIS

(76) Inventors: Robert A. Small, 3007 Dolphin Ct.; Walter J. Gaylor, 111 Wynwood Dr., both of Seabrook, TX (US) 77586

(*) Notice: Subject to any disclaimer, the term of this patent is extended or adjusted under 35 U.S.C. 154(b) by 0 days.

(21) Appl. No.: 09/161,059

(22) Filed: Sep. 25, 1998

Related U.S. Application Data

(60) Provisional application No. 60/059,958, filed on Sep. 25, 1997.

(51) Int. Cl.$^7$ .................. G01N 33/18; G01N 21/05
(52) U.S. Cl. .................. 422/78; 422/62; 422/63; 422/67; 422/82.05; 422/82.09; 436/43; 436/50; 436/145; 436/146; 436/155; 436/165; 436/180
(58) Field of Search .................. 422/62, 63, 67, 422/81, 82.05, 82.09, 100, 79, 104, 78.8; 436/43, 50, 145, 146, 164, 165, 180, 155; 73/861.41

(56) References Cited

U.S. PATENT DOCUMENTS

| | | | | |
|---|---|---|---|---|
| 3,308,648 | * | 3/1967 | Moulton et al. | 73/23.2 |
| 3,840,341 | | 10/1974 | Rogers. | |
| 3,994,423 | * | 11/1976 | Burg | 222/420 |
| 4,217,108 | * | 8/1980 | Melzer et al. | 422/79 |
| 4,277,438 | * | 7/1981 | Ejzak | 422/80 |
| 4,314,484 | * | 2/1982 | Bowman | 73/861.41 |
| 4,383,252 | * | 5/1983 | Purcell et al. | 340/606 |
| 4,678,913 | * | 7/1987 | Dodd, Jr. et al. | 250/339.05 |
| 4,680,977 | * | 7/1987 | Conero et al. | 73/861.41 |
| 4,820,281 | * | 4/1989 | Lawler Jr. | 604/253 |
| 4,869,722 | * | 9/1989 | Heyman | 604/253 |
| 4,936,828 | * | 6/1990 | Chiang | 604/65 |
| 5,045,069 | * | 9/1991 | Imparato | 604/253 |
| 5,088,990 | * | 2/1992 | Hivale et al. | 604/253 |
| 5,132,094 | | 7/1992 | Godec. | |
| 5,186,057 | * | 2/1993 | Everhart | 73/861.41 |
| 5,244,478 | | 9/1993 | Jolly. | |
| 5,292,666 | | 3/1994 | Fabinski. | |
| 5,312,756 | | 5/1994 | Jolly. | |

(List continued on next page.)

OTHER PUBLICATIONS

H. Liu et al, Anal. Chem. 1995, 67, 4221–4228, Dec. 1995.*
H. Liu et al., Anal. Chim. Acta 1996, 326, 13–22, Jun. 1996.*

*Primary Examiner*—Arlen Soderquist
(74) *Attorney, Agent, or Firm*—James L. Jackson; Mayor, Day, Caldwell & Keeton, LLP

(57) ABSTRACT

Apparatus and processes for water impurity analysis and for impurity analysis of various other liquids as well. Apparatus and processes are provided for physical characterization of liquid drops as a liquid sample builds up and then drops from a sample needle or other source. Liquid drop characterization is through utilization of infrared liquid drop measuring and computer modeling to measure a liquid drop as it builds up and then measures the falling liquid drop. By optically measuring an infrared radiated falling drop, and/or by characterizing the manner by which a sample drop is formed, a very precise way of determining the exact volume of a liquid sample is accomplished. Sample volume is typically directly proportional to concentration levels of the chemical constituent to be measured. By computer modeling, a falling drop can be quantified as to volume, rather than depending on the otherwise standard way of injecting a "known" volume. Infrared-emitting light is shone through a quartz window and is directed onto an infrared detector with an optical filter in the water vapor/liquid band, and measures not only the falling drop, but drop formation as it builds up. The infrared detector provides a signal output representing sample drop measurement, which signal output is input to a computer or microprocessor for processing and display.

6 Claims, 2 Drawing Sheets

U.S. PATENT DOCUMENTS

| | | | |
|---|---|---|---|
| 5,331,309 | * 7/1994 | Sakai | 340/606 |
| 5,411,052 | * 5/1995 | Murray | 137/392 |
| 5,413,763 | 5/1995 | Jeffers . | |
| 5,559,339 | * 9/1996 | Domanik et al. | 250/573 |
| 5,564,105 | 10/1996 | Alvino . | |
| 5,720,889 | 2/1998 | McBrayer . | |
| 5,766,959 | * 6/1998 | Dasgupta | 436/174 |

* cited by examiner

SAMPLE SIZE CHARACTERIZATION TECHNIQUE AND APPARATUS FOR LIQUID ANALYSIS

Applicants hereby claim the benefit of Provisional Application Serial No. 60/059,958, filed on Sep. 25, 1997 by Robert A. Small and Walter J. Gaylor and entitled Sample Size Characterization Technique And Apparatus For Liquid Analysis, which is incorporated by reference herein for all purposes.

BACKGROUND OF THE INVENTION

1. Field of the Invention

This invention relates generally to apparatus and processes for water impurity analysis and to impurity analysis of various other liquids as well. More particularly, the present invention concerns apparatus and processes for physical characterization of liquid drops as the liquid builds up and then drops from a sample needle or other source. Even more particularly the present invention is directed to liquid drop characterization through utilization of infrared liquid drop measuring and computer modeling to measure a liquid drop as it builds up and then to measure the falling liquid drop.

2. Description of the Prior Art

In many industrial and laboratory situations an authoritative test is needed for determining the degree of pollution that exists in a liquid, particularly water, stream. Water pollution due to the presence of organic materials has been measured indirectly in BOD analysis by how actively bacteria will use up the organic material in a given sample and consume oxygen from the sample. Since BOD analysis is an exceedingly slow procedure, it has been determined to be more appropriate to measure liquid samples directly for contamination due to the presence and volume of organic materials and to provide a system for rapid and low cost sample analysis. A low cost and rapid analysis process known as Total organic carbon (TOC) analysis has proven quite acceptable for this purpose. Moreover, TOC data can be readily converted to BOD or COD data if desired.

TOC analysis is typically conducted by injecting a known volume of water or other liquid into a furnace containing acid coated quartz chips and being at a sufficient temperature, 150° C., for example, to convert the inorganic carbon in the sample to $CO_2$ which is then measured by an infrared analyzer that is sensitive to $CO_2$. Another like volume from the same sample is then injected into a high temperature furnace, 950° C. for example, containing a catalyst to aid complete combustion. Oxygen is then metered into a reaction tube causing the total carbon, inorganic and organic, to be converted into $CO_2$. The volume of the $CO_2$ of the sample is then measured by an infrared analyzer. The $CO_2$ generated by complete combustion is directly proportional to the total carbon in the sample stream. A problem with TOC analysis of this nature is that inaccuracies can result from the coordination of two separate measurements, especially if the ratio of of inorganic carbon of the sample as compared to total carbon is large. The use of a catalyst can also create some problems from the standpoint of accuracy.

More recently, TOC analyzer manufacturers have introduced analyzers using a low-temperature ultra-violet (UV) promoted chemical oxidation method which offers certain advantages over combustion TOC analysis. These systems measure TOC directly be means of an acidification and scrubbing pretreatment system which removes carbonates prior to oxidation. The feasibility of UV/persulfate technique for oxidizing organic carbon was demonstrated a number of years ago and is well documented relative to its excellent oxidation efficiency. The major advantage of a low temperature UV promoted chemical TOC system is that all reactions take place in the liquid phase, resulting in increased reliability and reduced TOC analyzer maintenance requirements.

Total organic carbon (TOC) analysis is often considered beneficial as a rapid screening method to determine requirements of more costly and time-consuming specific toxic and other organic component analyses. In many cases, depending upon the application, TOC analysis is an adequate and inexpensive substitute for more time consuming and more expensive alternative methods for determination of water quality, provided the TOC analyzer being employed has sufficient sensitivity and capability. These more time consuming and expensive water quality determination methods, for example, include among others, the biochemical oxygen demand (BOD) test and the chemical oxygen demand (COD) test.

Although the low temperature UV promoted chemical TOC system has gained wide acceptance in the field of water quality testing, tests of the inventors has shown that TOC analysis of enhanced accuracy will result from physical characterization of liquid drops in connection with UV promoted chemical TOC analysis.

Thus, it is a feature of the present invention to provide methods and apparatus for accomplishing physical characterization of sample liquid drops as they build up relative to a known drop support structure;

It is another important feature of the present invention to provide for liquid drop characterization through utilization of infrared liquid drop measuring and computer modeling to measure a liquid drop as it builds up and then to measure the falling liquid drop.

Briefly considered, by optically (infrared light between 3.8 and 4.3 nanometers) measuring a falling drop, and/or by characterizing the manner by which a sample drop is formed, a very precise way of determining the exact volume of a liquid sample is accomplished. Very often, sample volume is directly proportional to concentration levels of the chemical constituent to be measured. By computer modeling a falling drop can be quantified as to volume, rather than depending on the otherwise standard way of injecting a "known" volume (which, through inaccuracies of sampling, may actually vary).

To accomplish sample drop characterization an infrared-emitting light is shone through a quartz window or a window composed of other suitable material and directed onto an infrared detector with an optical filter in the water vapor/liquid band, and measures not only the falling drop, but drop formation as it builds up. The infrared detector provides a signal output representing sample drop measurement, which signal output is input to a computer or microprocessor for processing and display, such as by a computer monitor, liquid crystal display, printer output, etc.

A liquid drop characterization head is provided which is mounted to a slide member, particularly a slide member composed of polytetrafluoroethylene or any other suitable substantially inert material which is movable between a drop characterization position, positions for conducting sample liquid into reactor ovens and a sample drain position. The liquid drop characterization head defines an upper, internally threaded opening that is in communication with the central passage having an infrared transparent tube, typically composed of quartz, sapphire or any other suitable infrared transparent material. A liquid drop supply, typically in the form of a needle is received by the internally threaded opening. The infrared transparent tube is positioned with its upper end within the central opening and with its external surface sealed to the head structure by an O-ring seal that is located within an O-ring groove. An infrared emitter is located within a lateral emitter receptacle of the head while an infrared detector is located within an oppositely located lateral detector receptacle in position to receive filtered infrared radiation which is altered by sample drop characterization and to output electrical signals responsive to drop characterization.

BRIEF DESCRIPTION OF THE DRAWINGS

So that the manner in which the above recited features, advantages and objects of the present invention are attained and can be understood in detail, a more particular description of the invention, briefly summarized above, may be had by reference to the preferred embodiment thereof which is illustrated in the appended drawings, which drawings are representative of a preferred embodiment of this invention and are incorporated as a part hereof.

It is to be noted however, that the appended drawings illustrate only a typical embodiment of this invention and are therefore not to be considered limiting of its scope, for the invention may admit to other equally effective embodiments.

In the Drawings:

FIG. 1 is a plan view of a liquid drop characterization head constructed in accordance with the present invention and representing the preferred embodiment of this invention;

FIG. 2 is a side elevational view in section, showing the liquid drop characterization head of FIG. 1, with internal openings and passages thereof being shown in broken line;

FIG. 3 is a fragmentary illustration shown in plan and representing intersection of the central cylindrical passage of the drop characterization head by a lateral receptacle being positioned for location of a light emitter in desired relation with the central passage;

FIG. 4 is a partial side view of the liquid drop characterization head of FIGS. 1–4 and further showing the configuration of the lateral receptacle;

Figure 5:
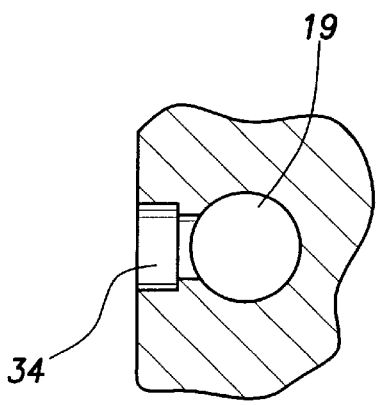
Figure 6:
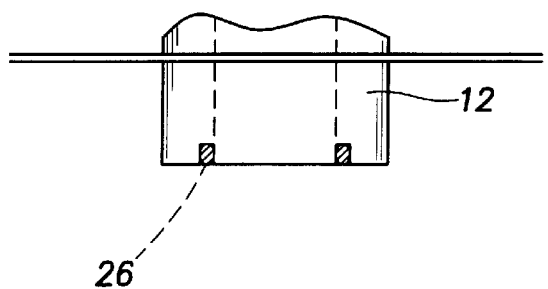
Figure 2:
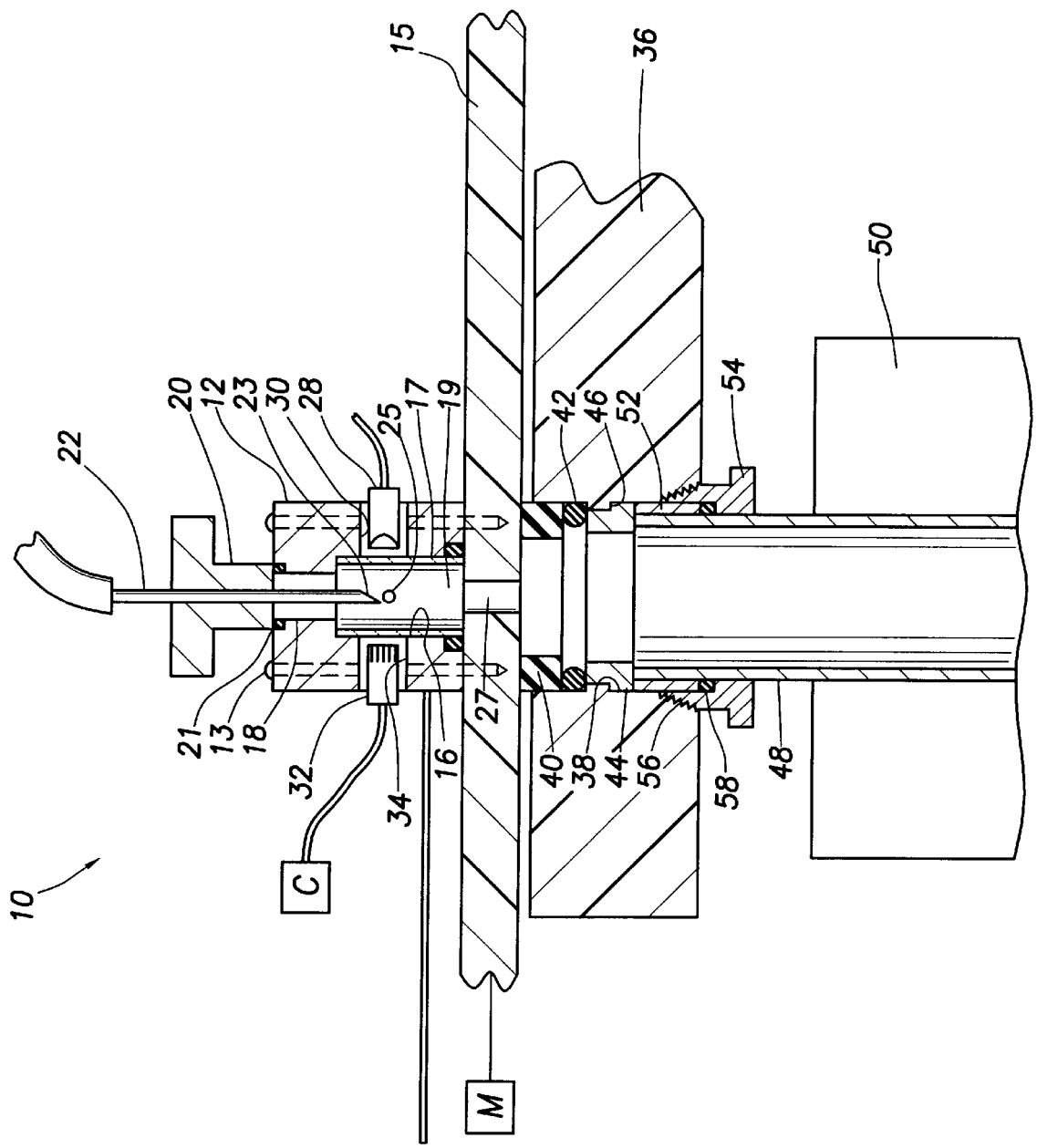

FIG. 5 is another partial sectional view, showing the opposite side of the liquid drop characterization head and showing the detector receptacle thereof within which is positioned a light detector in desired relation with the central passage; and FIG. 6 is a partial elevational view of the liquid drop characterization bead of FIGS. 1–5 and, by way of broken line, showing the central passage thereof and an O-ring groove being located about the central passage for receiving an O-ring seal for sealing the liquid drop characterization head to the upper end of a transparent tubular element that is positioned within the central passage of the head.

DETAILED DESCRIPTION OF PREFERRED EMBODIMENT

Figure 1:
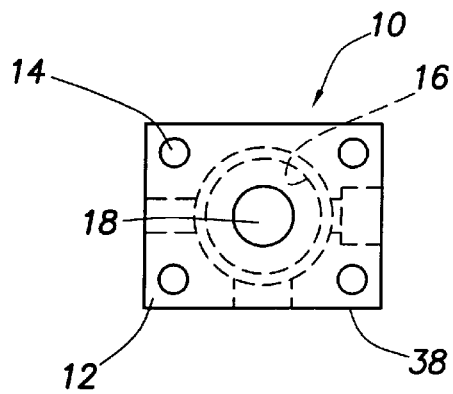
Figure 4:
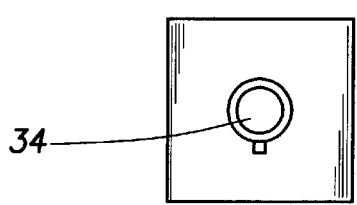
Figure 3:
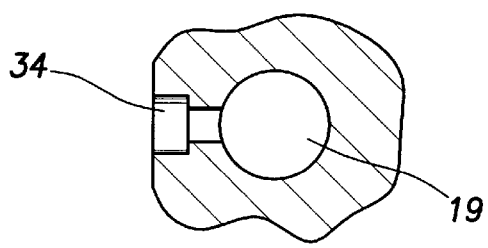

Referring now to the drawings and first to FIG. 1, a liquid drop characterization head is shown generally at 10 an incorporates a generally rectangular head block 12 defining screw apertures 14 at respective corners thereof to permit secure and stable mounting of the head block 12 with respect to any suitable structural support. Preferably, the head block 12 will be mounted by screws 13 to a slide member 15 that is composed of any suitable substantially inert material such as polytetrafluoroethylene or the like. The liquid drop characterization head defines an internal chamber 16 within which is located a suitable infrared filter 17, which is preferably composed of quartz, sapphire or any other suitable material. In accordance with the preferred embodiment of the present invention, the infrared filter 17 is in the form of a tubular element that is sized to closely fit the dimension of the central chamber 16 and, being tubular, defines a drop passage 19 through which sample drops descend en route to the reactor oven of the sample characterization and TOC analyzer system. The head block further defines an upper, internally threaded opening 18, as shown in FIG. 1, that is in communication with the central chamber 16 and the drop passage 19. A liquid drop supply fitting 20 is threaded within the internally threaded opening 18 and is sealed with respect to the head block 12 by an O-ring seal 21 which is received within a circular seal groove. A sample supply needle 22, connected to a sample feed tube, is mounted within the liquid drop supply fitting 20 and provides a drop discharge end 23 which is of a suitable geometry for sample liquid drop build-up to thus permit consistent build-up and release of sample liquid drops 25. When the sample drops descend from the needle they will fall through the internal chamber 16 and the passage 19 and then fall through a reactor feed opening 27 of the movable slide member 15.

The infrared filter 17 is in the form of an infrared transparent which tube is positioned with its upper end within the central chamber 16 and with its lower end sealed to the head block structure 12 by an O-ring seal 26 that is located within an O-ring groove of the head block structure as shown in the fragmentary view of FIG. 6. An infrared emitter 28 is located within a lateral emitter receptacle 30 of the head block structure 12, which intersects the central opening 16 while an infrared detector 32 is located within a lateral detector receptacle 34 that is defined within the sample drop characterization head and also intersects the central opening. The lateral detector receptacle 34 defines a slot 35 which permits predetermined orientation of the infrared detector to enable its accurate characterization of the forming and descending liquid sample drops. The infrared detector provides an electronic signal output responsive to detected infrared light which is input to a computer "C" for processing. The computer generated display, in the form of a CRT monitor, liquid crystal display, computer print-out, etc. will display the volume of the falling liquid sample drops and characterize sample drop build-up on the drop forming needle or other object responsive to computer processing.

Below the movable slide member is provided a valve body 36 which is preferably composed of any suitable substantially inert material such as polytetrafluoroethylene or the like which defines an opening 38 which is sealed with respect to the slide member 15 by means of a circular seal 40 and a circular sealing element 42. A circular seal retainer 44 is positioned within the opening 38 of the valve body by seating against an internal stop shoulder 46 of the valve body. The seal retainer provides support for the circular sealing element 42.

A reactor tube 48 extends upwardly from a reactor oven 50 and is positioned with its upper end shouldered against the seal retainer element 44. The reactor tube is sealed with respect to the valve body 50 by a friction sleeve 52 which is retained by a retainer nut 54 that is threaded into the lower internally threaded section 56 of the valve body opening 38. A circular seal element 58 retained within an internal seal groove of the retainer nut 54 maintains a seal between the reactor tube 48 and the retainer nut and valve body.

The slide member is movable from a position of alignment with the reactor tube 48 of the reactor oven 50 so that liquid samples for TOC analysis can be deposited within the reactor for complete combustion. To enhance productivity of sample drop characterization and TOC analysis, the slide member is driven linearly by a motor to selective positions of registry with one or more additional valve controlled reactor ovens which may be identical to reactor oven 50 and with a drain receptacle "D"

An infrared-emitting light from light emitter 28 is shone through the tubular quartz window 29 and is directed onto the infrared detector 32 with an optical filter in the water vapor/liquid band, and measures not only the falling drop, but drop formation as it builds up. The infrared detector produces an electronic signal output which is input to a computer "C" for processing. By optically (infrared light between 3.8 and 4.3 nanometers) measuring the falling liquid sample drop, a very precise way of determining the exact volume of sample is accomplished. Very often, sample volume is directly proportional to concentration levels of the chemical constituent to be measured. By computer modeling, a falling drop can be quantified as to volume, rather than depending on the otherwise standard way of injecting a "known" volume (which, through inaccuracies of sampling, may actually vary).

In view of the foregoing it is evident that the present invention is one well adapted to attain all of the objects and features hereinabove set forth, together with other objects and features which are inherent in the apparatus disclosed herein.

As will be readily apparent to those skilled in the art, the present invention may easily be produced in other specific forms without departing from its spirit or essential characteristics. The present embodiment is, therefore, to be considered as merely illustrative and not restrictive, the scope of the invention being indicated by the claims rather than the foregoing description, and all changes which come within the meaning and range of equivalence of the claims are therefore intended to be embraced therein.

We claim:

1. Apparatus for characterization of liquid sample drops during drop build-up and during descent thereof, comprising:
   (a) a sample drop characterization head defining an internal chamber and defining lateral emitter and detector receptacles intersecting said internal chamber and having a sample supply element for liquid sample drop build-up thereon and descent therefrom;
   (b) a tubular infrared transparent filter being located within said internal chamber of said sample drop characterization head and having opposed portions thereof exposed at said lateral emitter and detector receptacles;
   (c) an infrared light emitter being located within said lateral emitter receptacle of said sample drop characterization head and being positioned for directing infrared light through said infrared transparent filter, onto liquid sample drops during build-up thereof and through the path of descent of the liquid sample drops falling from said sample supply element;
   (d) at least one infrared light detector being located within said lateral detector receptacle of said sample drop characterization head and being positioned for receiving infrared light characterizing the liquid sample drops, said infrared light detector providing an electronic signal output representing characterization of the liquid sample drops during build-up and descent; and
   (e) means electronically processing said electronic signal output and providing a display representing characterization of the liquid sample drops during build-up and during descent.

2. The apparatus of claim 1, comprising:
   (a) a structural member having a drop opening therein;
   (b) said tubular infrared transparent filter defining a liquid sample drop passage permitting descending liquid sample drops from said sample supply element to fall through said liquid sample drop passage for infrared characterization thereof during build-up and descent and to fall through said drop opening.

3. Apparatus for characterization of liquid sample drops during drop build-up and during descent thereof, comprising:
   (a) a sample drop characterization head defining an internal chamber and having a sample supply element for liquid sample drop build-up thereon and descent therefrom;
   (b) an infrared transparent filter being located within said sample drop characterization head;
   (c) an infrared light emitter being supported by said sample drop characterization head and being positioned for directing infrared light through said infrared transparent filter, onto liquid sample drops during build-up thereof and through the path of descent of the liquid sample drops falling from said sample supply element;
   (d) infrared light detector means being supported by said sample drop characterization head and being positioned for receiving infrared light characterizing the liquid sample drops, said infrared light detector means providing an electronic signal output representing characterization of the liquid sample drops;
   (e) means electronically processing said electronic signal output and providing a display representing characterizing the liquid sample drops during build-up and during descent;
   (f) a movable slide element defining a reactor feed opening;
   (g) said drop characterization head being mounted to said movable slide element and being positioned for descent of falling liquid sample drops through said reactor feed opening; and
   (h) at least one total organic carbon analyzer reactor being positioned to receive liquid sample drops descending through said reactor feed opening.

4. The apparatus of claim 3, comprising:
   valve means for controlling admission of sample drops to said total organic carbon analyzer reactor.

5. Apparatus for characterization of liquid sample drops during drop build-up and during descent thereof, comprising:
   (a) a movable slide member defining a reactor feed opening;
   (b) a sample drop characterization head being mounted to said movable slide member and defining an internal chamber and having a sample supply element for liquid sample drop build-up thereon and descent therefrom, said sample supply element being oriented to drop liquid samples through said reactor feed opening;
   (c) an infrared transparent filter being located within said sample drop characterization head;
   (d) an infrared light emitter being supported by said sample drop characterization head and being positioned for directing infrared light through said infrared transparent filter, onto liquid sample drops during build-up thereof and through the path of descent of the liquid sample drops falling from said sample supply element;

(e) infrared light detector means being supported by said sample drop characterization head and being positioned for receiving infrared light characterizing the liquid sample drops, said infrared light detector means providing an electronic signal output representing characterization of the liquid sample drops; and (f) means electronically processing said electronic signal output and providing a display representing characterizing the liquid sample drops during build-up and during descent.

6. The apparatus of claim 5, wherein:

said infrared transparent filter being a tubular element located within said internal chamber and defining a liquid sample drop passage permitting descending liquid sample drops from said sample supply element to fall through said liquid sample drop passage for infrared characterization thereof during build-up and descent.

* * * * *